United States Patent
Ireland et al.

(10) Patent No.: US 7,278,983 B2
(45) Date of Patent: Oct. 9, 2007

(54) PHYSIOLOGICAL MONITORING DEVICE FOR CONTROLLING A MEDICATION INFUSION DEVICE

(75) Inventors: Jeffrey R. Ireland, Thousand Oaks, CA (US); Cary D. Talbot, Santa Clarita, CA (US); Mark C. Estes, Simi Valley, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 492 days.

(21) Appl. No.: 10/624,177

(22) Filed: Jul. 22, 2003

(65) Prior Publication Data

US 2004/0167464 A1    Aug. 26, 2004

Related U.S. Application Data

(60) Provisional application No. 60/398,213, filed on Jul. 24, 2002.

(51) Int. Cl.
*A61M 5/142* (2006.01)

(52) U.S. Cl. .................................... 604/66; 600/365

(58) Field of Classification Search .............. 604/66, 604/891.1, 67; 607/60, 2; 600/365
See application file for complete search history.

(56) References Cited

U.S. PATENT DOCUMENTS

| | | | |
|---|---|---|---|
| 3,631,847 A | 1/1972 | Hobbs, II | |
| 4,270,532 A | 6/1981 | Franetzki et al. | |
| 4,282,872 A | 8/1981 | Franetzki et al. | |
| 4,373,527 A | 2/1983 | Fischell | |
| 4,392,849 A | 7/1983 | Petre et al. | |
| 4,395,259 A | 7/1983 | Prestele et al. | |
| 4,433,072 A | 2/1984 | Pusineri et al. | |
| 4,443,218 A | 4/1984 | DeCant, Jr. et al. | |
| 4,469,481 A | 9/1984 | Kobayashi | |
| 4,475,901 A | 10/1984 | Kraegen et al. | |
| 4,494,950 A | 1/1985 | Fischell | |
| 4,529,401 A | 7/1985 | Leslie et al. | |

(Continued)

FOREIGN PATENT DOCUMENTS

DE    4329229    3/1995

(Continued)

OTHER PUBLICATIONS

PCT/US03/23018 International Search Report mailed Nov. 11, 2003.

(Continued)

*Primary Examiner*—Nicholas D. Lucchesi
*Assistant Examiner*—Laura Bouchelle
(74) *Attorney, Agent, or Firm*—William K. Konrad; Konrad Raynes & Victor LLP

(57) ABSTRACT

Methods and apparatuses for calculating and transmitting medication dosage or bolus information are provided. A blood glucose meter receives a test strip with a sample of the user's blood and measures the user's blood glucose level with a sensor. The meter then calculates a bolus amount that is transmitted to a medication infusion pump using a radio frequency transmitter or transceiver. The infusion pump receives the bolus amount data and then delivers a bolus of medication to the user based on the calculated bolus estimate. The meter may also transmit commands to, and be used to remotely control, the infusion pump.

40 Claims, 6 Drawing Sheets

U.S. PATENT DOCUMENTS

| | | |
|---|---|---|
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,696,671 A | 9/1987 | Epstein et al. |
| 4,703,756 A | 11/1987 | Gough et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,865,584 A * | 9/1989 | Epstein et al. ............... 604/67 |
| 4,871,351 A | 10/1989 | Feingold |
| 4,898,578 A | 2/1990 | Rubalcaba, Jr. |
| 4,935,105 A | 6/1990 | Churchouse |
| 4,953,552 A | 9/1990 | DeMarzo |
| 5,019,974 A | 5/1991 | Beckers |
| 5,034,004 A | 7/1991 | Crankshaw |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,113,869 A | 5/1992 | Nappholz et al. |
| 5,153,827 A | 10/1992 | Coutre et al. |
| 5,165,407 A | 11/1992 | Wilson et al. |
| 5,211,626 A | 5/1993 | Frank et al. |
| 5,216,597 A | 6/1993 | Beckers |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,266,013 A | 11/1993 | Aubert et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,319,363 A | 6/1994 | Welch et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,364,346 A | 11/1994 | Schrezenmeir |
| 5,368,562 A | 11/1994 | Blomquist et al. |
| 5,370,622 A | 12/1994 | Livingston |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,417,222 A | 5/1995 | Dempsey et al. |
| 5,429,602 A | 7/1995 | Hauser |
| 5,437,634 A | 8/1995 | Amano |
| 5,464,392 A | 11/1995 | Epstein et al. |
| 5,472,317 A | 12/1995 | Field et al. |
| 5,478,211 A | 12/1995 | Dominiak et al. |
| 5,482,446 A | 1/1996 | Williamson et al. |
| 5,482,473 A | 1/1996 | Lord et al. |
| 5,485,408 A | 1/1996 | Blomquist |
| 5,497,772 A | 3/1996 | Schulman et al. |
| 5,499,243 A | 3/1996 | Hall |
| 5,507,288 A | 4/1996 | Bocker et al. |
| 5,543,326 A | 8/1996 | Heller et al. |
| 5,545,191 A | 8/1996 | Mann et al. |
| 5,558,640 A | 9/1996 | Pfeiler et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,584,814 A | 12/1996 | Schuster et al. |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,609,575 A | 3/1997 | Larson et al. |
| 5,616,124 A | 4/1997 | Hague et al. |
| 5,620,312 A | 4/1997 | Hyman et al. |
| 5,626,144 A | 5/1997 | Tacklind et al. |
| 5,630,710 A | 5/1997 | Tune et al. |
| 5,643,212 A | 7/1997 | Coutre et al. |
| 5,647,853 A | 7/1997 | Feldmann et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,681,285 A | 10/1997 | Ford et al. |
| 5,685,844 A | 11/1997 | Marttila |
| 5,687,734 A | 11/1997 | Dempsey et al. |
| 5,704,366 A | 1/1998 | Tacklind et al. |
| 5,713,856 A | 2/1998 | Eggers et al. |
| 5,748,103 A | 5/1998 | Flach et al. |
| 5,750,926 A | 5/1998 | Schulman et al. |
| 5,764,159 A | 6/1998 | Neftel |
| 5,772,635 A | 6/1998 | Dastur et al. |
| 5,777,060 A | 7/1998 | Van Antwerp |
| 5,779,665 A | 7/1998 | Mastrototaro et al. |
| 5,786,439 A | 7/1998 | Van Antwerp et al. |
| 5,788,669 A | 8/1998 | Peterson |
| 5,791,344 A | 8/1998 | Schulman et al. |
| 5,807,336 A | 9/1998 | Russo et al. |
| 5,814,015 A | 9/1998 | Gargano et al. |
| 5,832,448 A | 11/1998 | Brown |
| 5,840,020 A | 11/1998 | Heinonen et al. |
| 5,840,026 A | 11/1998 | Uber, III et al. |
| 5,861,018 A | 1/1999 | Feierbach |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown et al. |
| 5,904,708 A | 5/1999 | Goedeke |
| 5,913,310 A | 6/1999 | Brown |
| 5,917,346 A | 6/1999 | Gord et al. |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,951,521 A | 9/1999 | Mastrototaro et al. |
| 5,956,501 A | 9/1999 | Brown |
| 5,960,403 A | 9/1999 | Brown |
| 5,961,451 A | 10/1999 | Reber et al. |
| 5,965,380 A | 10/1999 | Heller et al. |
| 5,972,199 A | 10/1999 | Heller et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,067,474 A | 5/2000 | Schulman et al. |

| | | |
|---|---|---|
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,135,949 A | 10/2000 | Russo et al. |
| 6,142,008 A | 11/2000 | Cole et al. |
| 6,143,164 A | 11/2000 | Heller et al. |
| 6,162,611 A | 12/2000 | Heller et al. |
| 6,171,276 B1 | 1/2001 | Lippe et al. |
| 6,175,752 B1 | 1/2001 | Say et al. |
| 6,246,992 B1 | 6/2001 | Brown |
| 6,248,067 B1 | 6/2001 | Causey et al. |
| 6,250,309 B1 | 6/2001 | Krichen et al. |
| 6,254,586 B1 | 7/2001 | Mann et al. |
| 6,259,937 B1 | 7/2001 | Schulman et al. |
| 6,269,340 B1 | 7/2001 | Ford et al. |
| 6,270,478 B1 | 8/2001 | Mernoe |
| 6,270,481 B1 | 8/2001 | Mason et al. |
| 6,295,506 B1 | 9/2001 | Heinonen et al. |
| 6,329,161 B1 | 12/2001 | Heller et al. |
| 6,355,018 B1 | 3/2002 | Vasko |
| 6,461,331 B1 | 10/2002 | Van Antwerp |
| 6,472,122 B1 | 10/2002 | Schulman et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,551,276 B1 | 4/2003 | Mann et al. |
| 6,554,798 B1 | 4/2003 | Mann et al. |
| 6,556,963 B1 | 4/2003 | Tetzlaff |
| 6,558,320 B1 | 5/2003 | Causey, III et al. |
| 6,560,471 B1 | 5/2003 | Heller et al. |
| 6,565,509 B1 | 5/2003 | Say et al. |
| 6,579,690 B1 * | 6/2003 | Bonnecaze et al. ............ 435/14 |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,671,554 B2 | 12/2003 | Gibson et al. |
| 6,676,816 B2 | 1/2004 | Mao et al. |
| 6,689,091 B2 | 2/2004 | Bui et al. |
| 6,689,265 B2 | 2/2004 | Heller et al. |
| 6,733,471 B1 | 5/2004 | Ericson et al. |
| 6,746,582 B2 | 6/2004 | Heller et al. |
| 6,749,740 B2 | 6/2004 | Liamos et al. |
| 6,809,653 B1 | 10/2004 | Mann et al. |
| 6,872,200 B2 | 3/2005 | Mann et al. |
| 6,881,551 B2 | 4/2005 | Heller et al. |
| 6,893,545 B2 | 5/2005 | Gotoh et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,936,029 B2 | 8/2005 | Mann et al. |
| 6,942,518 B2 | 9/2005 | Liamos et al. |
| 6,945,760 B2 | 9/2005 | Gray et al. |
| 6,979,326 B2 | 12/2005 | Mann et al. |
| 6,997,920 B2 | 2/2006 | Mann et al. |
| 7,025,743 B2 | 4/2006 | Mann et al. |
| 2002/0019606 A1* | 2/2002 | Lebel et al. .................. 604/66 |
| 2002/0082665 A1 | 6/2002 | Haller et al. |
| 2002/0161288 A1 | 10/2002 | Shin et al. |
| 2003/0078560 A1 | 4/2003 | Miller et al. |
| 2003/0088166 A1 | 5/2003 | Say et al. |
| 2003/0152823 A1 | 8/2003 | Heller et al. |
| 2003/0168338 A1 | 9/2003 | Liamos et al. |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0074785 A1 | 4/2004 | Holker et al. |
| 2004/0093167 A1 | 5/2004 | Braig et al. |
| 2004/0111017 A1 | 6/2004 | Say et al. |
| 2005/0214585 A1 | 9/2005 | Bernatz et al. |

FOREIGN PATENT DOCUMENTS

| | | |
|---|---|---|
| EP | 0098592 | 1/1984 |
| EP | 0680727 | 11/1995 |
| EP | 0806738 | 11/1997 |
| EP | 0880936 | 12/1998 |
| EP | 1048264 | 11/2000 |
| EP | 1338295 | 8/2003 |
| GB | 2218831 | 11/1989 |
| WO | 9528878 | 11/1995 |
| WO | 9620745 | 7/1996 |
| WO | 9636389 | 11/1996 |
| WO | 9637246 | 11/1996 |
| WO | 9721456 | 6/1997 |
| WO | 9728736 | 8/1997 |
| WO | 9800056 | 1/1998 |
| WO | 9820439 | 5/1998 |
| WO | 9824358 | 6/1998 |
| WO | 9842407 | 10/1998 |
| WO | 9849659 | 11/1998 |
| WO | 9856293 | 12/1998 |
| WO | 9859487 | 12/1998 |
| WO | 9908183 | 2/1999 |
| WO | 9910801 | 3/1999 |
| WO | 9918532 | 4/1999 |
| WO | 9922236 | 5/1999 |
| WO | 9945375 | 9/1999 |
| WO | 9945387 | 9/1999 |
| WO | 9956613 | 11/1999 |
| WO | 0010628 | 3/2000 |
| WO | 0019887 | 4/2000 |
| WO | 0029047 | 5/2000 |
| WO | 0047109 | 8/2000 |
| WO | 0078210 | 12/2000 |
| WO | 0128416 | 4/2001 |
| WO | 0128495 | 4/2001 |
| WO | 0139089 | 5/2001 |
| WO | 0152718 | 7/2001 |
| WO | 0152727 | 7/2001 |
| WO | 0156454 | 8/2001 |
| WO | 0258537 | 8/2002 |

OTHER PUBLICATIONS

Abel, P. et al., "Experience with an Implantable Glucose Sensor as a Prerequisite of an Artificial Beta Cell", Biomed. Biochim., 1984, Acta 43, 5, pp. 577-584.

Bode, B.W. et al., "Reduction in Severe Hypoglycemia with Long-Term Continuous Subcutaneous Insulin Infusion in Type I Diabetes", Diabetes Care, vol. 19, No. 4, 1996, 324-327.

Boland, E., "Teens Pumping it Up! Insulin Pump Therapy Guide for Adolescents", 2nd Edition, 1998, 60 pp.

Brackenridge, B.P., "Carbohydrate Gram Counting: A Key to Accurate Mealtime Boluses in Intensive Diabetes Therapy", Practical Diabetology, vol. 11, No. 2, 1992, pp. 22-28.

Brackenridge, B.P. et al., "Counting Carbohydrates: How to Zero in on Good Control using the MiniMed insulin Pump", MiniMed Technologies Inc., 1995, 26 pp.

Farkas-Hirsch, R. et al., "Continuous Subcutaneous Insulin Infusion: A Review of the Past and Its Implementation for the Future", Diabetes Spectrum From Research to Practice, vol. 7, No. 2, 1994, pp. 80-84 and 136-138.

Hirsch, I.B. et al., "Intensive Insulin Therapy for Treatment of Type I Diabetes", Diabetes Care, vol. 13, No. 12, 1990, pp. 1265-1283.

Kawamori, R. et al., "Perfect Normalization of Excessive Glucagon Responses to Intravenous Arginine in Human Diabetes Mellitus with the Artificial Beta-Cell", Rapid Publication from Diabetes, vol. 29, Sep. 1980, pp. 762-765.

Kulkarni, K. et al., "Carbohydrate Counting: A Primer for Insulin Pump Users to Zero in on Good Control", MiniMed Inc., 1999, pp. 1-50.

Marcus, A.O. et al., "Insulin Pump Therapy: Acceptable Alternative to Injection Therapy", Postgraduate Medicine, vol. 99, No. 3, 1996, pp. 125-143.

Mastrototaro, J.J. et al., "An Electroenzymatic Sensor Capable of 72 Hour Continuous Monitoring of Subcutaneous Glucose", Presentation given at the 14th International Diabetes Federation Congress in Washington, D.C., Jun. 1991, 19 pp.

McKean, B., et al., "A Telemetry-Instrumentation System for Chronically Implanted Glucose and Oxygen Sensors", IEEE Transactions on Biomedical Engineering, vol. 35, No. 7, Jul. 1988, pp. 526-532.

MiniMed, Inc., "MiniMed 508 Insulin Pump Flipchart: Guide to Insulin Pump Therapy", Dec. 1999, 35 pp.

MiniMed, Inc., "MiniMed 508 Insulin Pump User's Guide", Sep. 2001, pp. 1-145.

MiniMed, Inc., "MiniMed Dosage Calculator", 1994, 4 pp.

MiniMed, Inc., "Now I Can: Correction Bolus Calculator and Meal Bolus Calculator", Jul. 2000, 2 pp.

MiniMed, Inc., "Medtronic MiniMed Meal Bolus Calculator and Correction Bolus Calculator", International Version, Feb. 2002, 4 pp.

MiniMed, Inc., "Now I Can: MiniMed Pump Therapy Brochure", Sep. 2000, 10 pp.

MiniMed, Inc., "Now I Can: MiniMed Diabetes Management Packet", Sep. 2000, 46 pp.

MiniMed, Inc., "Paradigm Infusion Pump: Model MMT-511 User Guide", Jan. 2002, 83 pp.

Monroe, D. et al., "Novel implantable glucose sensors", ACL, Dec. 1989, pp. 8-16.

Nishida, K. et al., "Clinical applications of the wearable artificial endocrine pancreas with the newly designed needle-type glucose sensor", Elsevier Science B.V., 1994, pp. 353-358.

Reed, J, "Living with Diabetes", Voice of the Diabetic, vol. 11, No. 3, 1996, pp. 1-38.

Shichiri, M. et al., "A Needle-Type Glucose Sensor—A Valuable Tool Not Only for a Self-Blood Glucose Monitoring But for a Wearable Artificial Pancreas-", Life Support Systems, Proceedings XI Annual Meeting ESAO, Sep. 1984, vol. 2, Supplement 1, pp. 7-9.

Shichiri, M. et al., "An Artificial Endocrine Pancreas—Problems Awaiting Solution for Long-Term Clinical Applications of a Glucose Sensor", Frontiers Med. Biol. Engng, VSP, vol. 3, No. 4, 1991, pp. 283-292.

Shichiri, M. et al., "Closed-Loop Glycemic Control with a Wearable Artificial Endocrine Pancreas Variations in Daily Insulin Requirements to Glycemic Response", Rapid Publication from Diabetes, vol. 33, Dec. 1984, pp. 1200-1202.

Shichiri, M. et al., "Glycaemic Control in Pancreatectomized Dogs with a Wearable Artificial Endocrine Pancreas", Diabetologia 24, 1983, pp. 179-184.

Shichiri, M. et al., "Normalization of the Paradoxic Secretion of Glucagon in Diabetics Who Were Controlled by the Artifical Beta Cell", Diabetes, vol. 28, Apr. 1979, pp. 272-275.

Shichiri, M. et al., "Telemetry Glucose Monitoring Device with Needle-Type Glucose Sensor: A Useful Tool for Blood Glucose Monitoring in Diabetic Individuals", Diabetes Care, vol. 9, No. 3, May-Jun. 1986, pp. 298-301.

Shichiri, M. et al., "The Wearable Artificial Endocrine Pancreas with a Needle-Type Glkucose Sensor: Perfect Glycemic Control in Ambulatory Diabetics", Acta Paediatr Jpn 26, 1984, pp. 359-370.

Shichiri, M. et al., "Wearable Artificial Endocrine Pancreas with Needle-Type Glucose Sensor", The Lancet, Nov. 20, 1982, pp. 1129-1131.

Shults, M.C. et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.

Skyler, J.S., "Continuous Subcutaneous Insulin Infusion [CSII] With External Devices: Current Status", Update in Drug Delivery Systems, Futura Publishing Company, Chapter 13, 1989, pp. 163-183.

Strowig, S.M., "Initiation and Management of Insulin Pump Therapy", The Diabetes Educator, vol. 19, No. 1, 1993, pp. 50-60.

Walsh, J. et al., "Pumping Insulin: The Art of Using an Insulin Pump", MiniMed Technologies, 1989, 149 pp.

Wang, J. et al:, "Needle-Type Dual Microsensor for the Simultaneous Monitoring of Glucose and Insulin", Analytical Chemistry, vol. 73, No. 4, Feb. 15, 2001, pp. 844-847.

Fredrickson, L. (Ed.), "The Insulin Pump Therapy Book: Insights from the Experts", MiniMed Technologies, 1995, 172 pp.

Banks, P. (Ed.), "Insulin Infusion Pump Therapy", Intensive Diabetes Management, 1995, pp. 66-78.

* cited by examiner

PHYSIOLOGICAL MONITORING DEVICE FOR CONTROLLING A MEDICATION INFUSION DEVICE

CROSS REFERENCE TO RELATED APPLICATIONS

This application claims priority from U.S. Provisional Application No. 60/398,213, filed Jul. 24, 2002.

FIELD OF THE INVENTION

This invention relates generally to improvements in medical devices, such as patient physiological monitoring systems and medication infusion systems that are used for controlled delivery of medication to a user. More specifically, this invention relates to improved methods and apparatuses for calculating and communicating the quantity or bolus of medication that is to be delivered to the user.

BACKGROUND

People with Type 1 diabetes and some with Type 2 diabetes use insulin to control their blood glucose (BG) level. Typically, if a person's BG level is too high, he or she can inject a "bolus" (dose) of insulin to lower his/her BG level to a desired target level. Furthermore, he or she may inject a bolus of insulin in anticipation of ingesting carbohydrates, thus heading off a sharp rise in BG level.

Various calculations can be used to determine the amount of insulin to inject, and bolus estimation software is available for performing such calculations. These software programs can be used on an electronic computing device, such as a computer, the Internet, a personal digital assistant (PDA), or an insulin delivery device. Insulin delivery devices include infusion pumps, injection pens, and IV meters.

Some bolus estimation software takes into account an individual's current BG level. Presently, blood glucose can be measured using devices such as a test strip meter, a continuous glucose measurement system, a hospital hemocue, or an automated intermittent blood glucose measurement system. BG measurement devices use various methods, such as a sample of blood, a sensor in contact with a bodily fluid, an optical sensor, an enzymatic sensor, or a fluorescent sensor.

When the BG measurement device has generated a measurement, it is displayed on the device. Then the user may visually read the BG measurement and physically enter it into an electronic computing device to calculate a bolus estimate. Finally, once the bolus estimate is calculated, the user can inject the insulin bolus, or can program an insulin delivery device to deliver the bolus into his/her body.

Unfortunately, this process can be cumbersome and subject to transcribing errors—for example, the user may not accurately enter the BG measurement that is displayed on the BG measurement device into the electronic computing device. Thus if the BG measurement is not entered correctly, the bolus estimate may not be accurate. Furthermore, once the bolus estimation calculation is complete, the user may not accurately enter the bolus amount into a programmable infusion device, or the user may read the bolus amount incorrectly and inject the wrong amount of medication.

SUMMARY OF THE ILLUSTRATED EMBODIMENTS

A physiological monitoring device that conducts a bolus estimation calculation is provided. In one aspect, the monitoring device communicates a bolus amount resulting from the bolus estimation calculation to a medication infusion device, which delivers a bolus of medication to a user based on the communication from the monitoring device. The medication infusion device delivers the medication automatically after receiving the communication from the monitoring device.

In another aspect, the monitoring device comprises a processor and a sensor coupled to the processor and adapted to provide an output signal as a function of a concentration of an analyte in the user. A communication circuit is coupled to the processor. The processor is adapted to calculate an amount of the medication or fluid to be infused into the user's body based upon the sensor output signal, and to cause the monitoring device communication circuit to transmit a set of data indicative of the amount of the fluid to be infused.

An indicator is coupled to the monitoring device processor and adapted to provide a notification of the following events: the measuring of the output signal produced by the sensor, the calculating of the amount of the fluid, and the transmitting of the set of data by the first communication circuit.

The medication infusion device comprises a processor and a drive mechanism coupled to the processor and adapted to infuse the fluid into the user's body. A communication circuit is coupled to the processor and adapted to receive the set of data from the monitoring device communication circuit. The processor is adapted to cause the drive mechanism to automatically infuse the fluid into the user in accordance with the set of data.

In another aspect, the monitoring device communication circuit is a transmitter or a transceiver, and the infusion device communication circuit is a receiver or a transceiver.

In an alternative embodiment, the monitoring device further comprises a user input device for inputting commands. The monitoring device communication circuit transmits the first set of data in response to a command from the input device.

In another aspect, the monitoring device processor is further adapted to determine a first amount of time that has elapsed since the sensor provided the output signal and to cause the monitoring device communication circuit to transmit the first set of data if the first amount of time does not exceed a predetermined amount of time.

In yet another embodiment, the monitoring device further comprises an indicator coupled to the monitoring device processor and adapted to provide a display of the amount of the fluid and a user input device for inputting commands. The monitoring device processor is further adapted to cause the monitoring device communication circuit to transmit the first set of data in response to a first command from the input device.

In another aspect, the infusion device further comprises a user input device for inputting commands and an indicator coupled to the infusion device processor and adapted to provide a display of the amount of the fluid. An infusion device memory is coupled to the infusion device processor and adapted to store at least two fluid infusion parameters. The infusion device processor is further adapted to retrieve one of the fluid infusion parameters from the memory in response to a command from the input device associated with a selection by the user. The infusion device processor further causes the drive mechanism to infuse the fluid into the user's body in accordance with the first or second fluid infusion parameter.

In an alternative embodiment, the monitoring device processor is further adapted to cause the monitoring device communication circuit to transmit a first command repeatedly for a plurality of transmissions and the infusion device communication circuit is further adapted to receive the first command. The infusion device processor is further adapted to cause power to the infusion device communication circuit to be cycled whereby the power is removed from the infusion device communication circuit for a first time period and is restored to the infusion device communication circuit for a second time period. The infusion device processor causes the power to the infusion device communication circuit to be restored and the power cycling to be discontinued if the first command has been received.

In yet another embodiment, the monitoring device sensor is coupled to the monitoring device processor and adapted to provide first and second output signals as a function of first and second quantities of an analyte in the user. The monitoring device processor is adapted to calculate a first amount of the fluid to be infused into the user's body based upon the first output signal and generate a first code associated with the first amount of the fluid. The processor then causes the monitoring device telemetry circuit to transmit a first plurality of transmissions wherein each of the first plurality of transmissions is comprised of a first set of data and the first code, the first set of data being indicative of the first amount of the fluid.

The monitoring device processor then calculates a second amount of the fluid to be infused into the user's body based upon the second output signal and generates a second code associated with the second amount of the fluid. The processor next causes the monitoring device telemetry circuit to transmit a second plurality of transmissions wherein each of said second plurality of transmissions is comprised of a second set of data and the second code, the second set of data being indicative of the second amount of the fluid.

The infusion device telemetry circuit is adapted to receive the first and second plurality of transmissions from the monitoring device telemetry circuit. The infusion device processor is adapted to store a first received code, said first received code being the first code or the second code as received from one of the first or second plurality of transmissions. The processor then compares a second received code with the first received code, where the second received code is another of the first or second codes as received from another of the first or second plurality of transmissions. The processor then causes the drive mechanism to apply pressure to the fluid in accordance with the second set of data if the second received code does not equal the first received code.

In one aspect, the first code is generated by incrementing a counter to provide a first counter value and the second code is generated by incrementing the counter to provide a second counter value. In another aspect, the first code corresponds to a first date and time and the second code corresponds to a second date and time.

There are additional aspects to the present inventions. It should therefore be understood that the preceding is merely a brief summary of some embodiments and aspects of the present inventions. Additional embodiments and aspects of the present inventions are referenced below. It should further be understood that numerous changes to the disclosed embodiments can be made without departing from the spirit or scope of the inventions. The preceding summary therefore is not meant to limit the scope of the inventions. Rather, the scope of the inventions is to be determined by appended claims and their equivalents.

DETAILED DESCRIPTION OF THE PREFERRED EMBODIMENTS

In the following description, reference is made to the accompanying drawings which form a part hereof and which illustrate several embodiments of the present invention. It is understood that other embodiments may be used and structural and operational changes may be made without departing from the scope of the present invention.

A physiological monitoring device that conducts a bolus estimation calculation is provided. In one aspect, the monitoring device communicates a bolus amount resulting from the bolus estimation calculation to a medication infusion device, which then delivers a bolus of medication to a user based on the communication from the monitoring device. The monitoring device may also be used to control other functions of the medication infusion device based on communications from the monitoring device.

Figure 1:
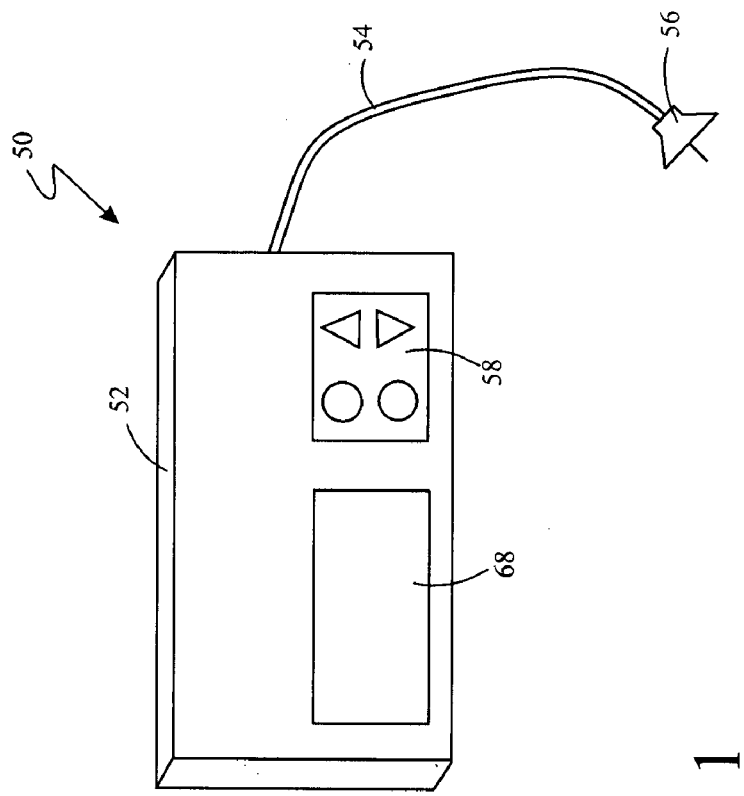
FIG. 1 is a perspective view of a blood glucose monitor and an infusion pump in accordance with an embodiment of the present invention.
Figure 1:
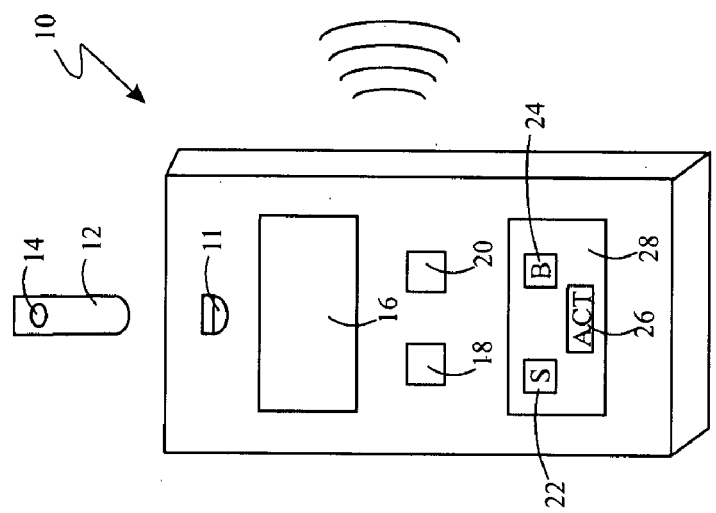
Figure 4A:
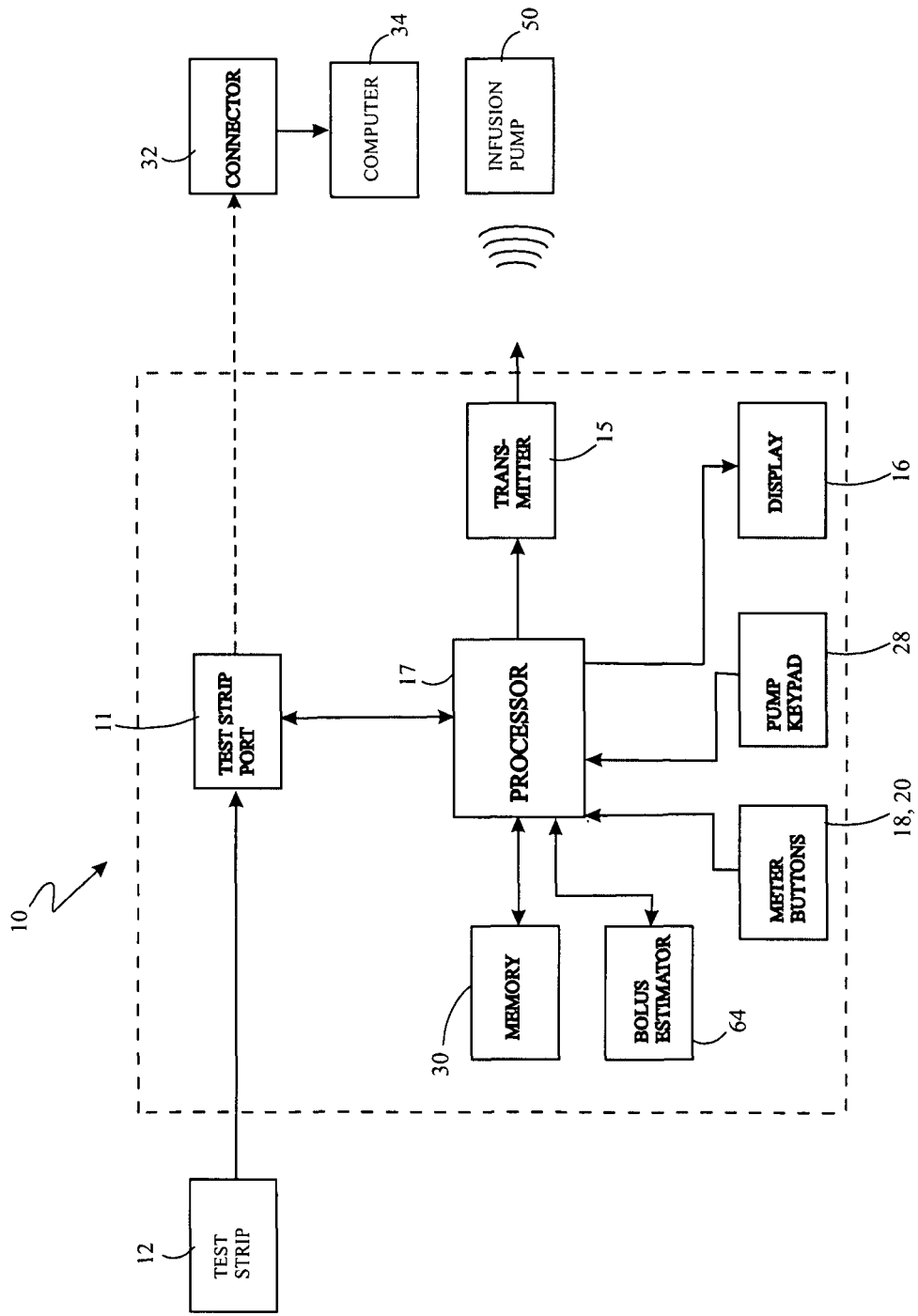
FIG. 4a is a simplified block diagram of a blood glucose monitor in accordance with an embodiment of the present invention.

Referring to FIGS. 1 and 4a, the monitoring device is a BG test strip meter 10 and the medication infusion device is a medication infusion pump 50, such as for example, an insulin infusion pump. The BG meter 10 receives a test strip 12 with a sample 14 of the user's blood and measures the user's BG level with a sensor. The BG meter 10 then calculates a bolus amount that is transmitted to the infusion pump 50, for example, using a radio frequency (RF) transmitter or transceiver. The infusion pump 50 then delivers a bolus of medication to the user based on the bolus amount data received from the BG meter 10. Transmission of the bolus amount from the BG meter 10 to the infusion pump 50 may eliminate user transcription errors and simplify the use of a bolus estimator.

In particular embodiments, the physiological monitoring device is the BG meter 10 which includes a test strip receptacle or port 11 for receiving and analyzing the test strip 12 with the sample 14 of the user's blood to obtain a BG measurement. In alternative embodiments, the monitoring device may be a continuous glucose measurement system, a hospital hemocue, or an automated intermittent blood glucose measurement system. For example, the monitoring device may generally be of the type or include features disclosed in U.S. Pat. No. 6,558,320, U.S. Patent Application Publication No. 20020002326, published on Jan. 3, 2003, and U.S. patent application Ser. No. 09/377,472 filed Aug. 19, 1999 and entitled "Telemetered Characteristic Monitor System and Method of Using the Same," and Ser. No. 09/334,996 filed Jun. 17, 1999 and entitled "Characteristic Monitor with a Characteristic Meter and Method of Using the Same," which are herein incorporated by reference. Moreover, the monitoring device may use other methods or sensors for measuring the user's BG level, such as a sensor in contact with a body fluid, an optical sensor, an enzymatic sensor, a fluorescent sensor, or a blood sample placed in a receptacle. Some monitoring devices are adapted to be carried by a user during his or her daily activities, and thus, may be implanted within the body of the user, or may be external to the user's body and hand-held, or held in a clothing pocket or attached to the body or clothing by straps, adhesives, fasteners, etc.

In further alternative embodiments, the monitoring device may use samples from body fluids other than blood, such as interstitial fluid, spinal fluid, saliva, urine, tears, or sweat. Other physiological determining or measuring devices may be used to determine or measure the concentrations or quantities of other characteristics, analytes, or agents in the user, such as hormones, cholesterol, medication concentrations, viral loads (e.g., HIV), lactose, oxygen, pH, heart rate, respiratory rate, etc. which may be used in a bolus estimation algorithm or may be used to identify an alarm condition or record an event.

Referring again to FIGS. 1 and 4a, the BG meter 10 includes a bolus estimator 64 that is comprised of software algorithms. Once the BG meter 10 obtains a BG measurement, the bolus estimator 64 uses the measurement data to calculate a bolus amount. The bolus amount data is transmitted to the infusion pump 50 using a radio frequency (RF) transmitter 15, as will be described below. Alternatively, the RF transmitter 15 may be replaced with an RF transceiver 19 (as shown in FIG. 4b) or 36 (as shown in FIG. 5), and the bolus data may be transmitted to the infusion pump 50 using the RF transceiver 19 or 36.

In the illustrated embodiment, the test strip port 11 and RF transmitter 15 are coupled to a processor 17, which executes programs (including the bolus estimator 64) and controls the BG meter 10. The processor 17 is also connected to a memory 30 for storing programs, history data, user defined information and parameters. The BG meter 10 also includes an indicator or display 16 for providing notifications to the user of the BG measurement, bolus amount information, and messages, such as status, alarms or error messages. In particular embodiments, the display 16 includes a backlight for reading the display 16 in the dark.

The BG meter 10 includes user input devices comprising one or more housing buttons 18 and 20 for control of the meter 10, such as turning it on or off, reviewing previous BG measurements or bolus amounts, transmitting bolus data to the infusion pump 50, and turning off the transmitter 15 (or transceiver 19 (shown in FIG. 4b) or 36 (shown in FIG. 5)) in the BG meter 10 so that it does not send bolus data to the infusion pump 50.

Figure 4B:
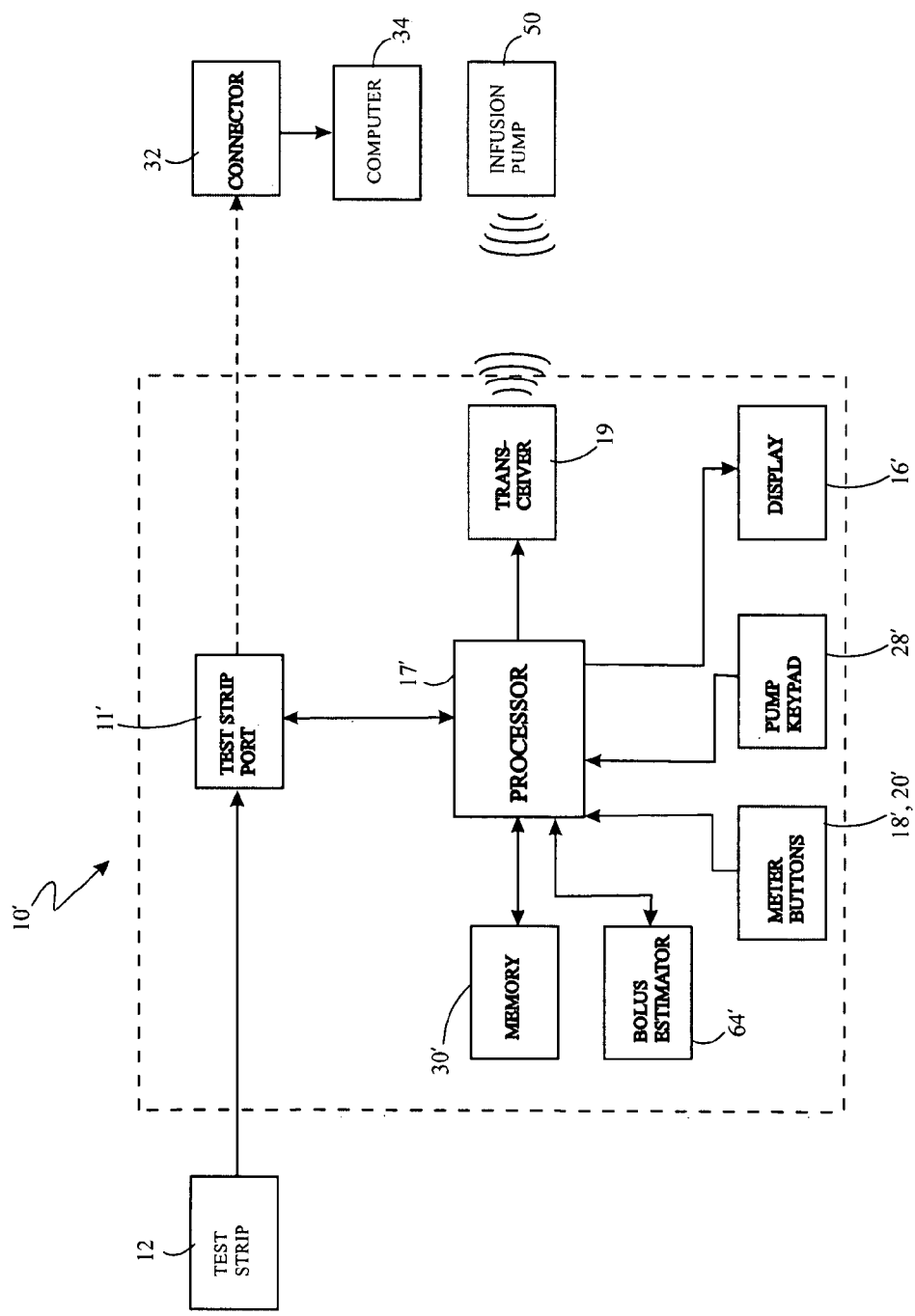
FIG. 4b is a simplified block diagram of a blood glucose monitor in accordance with another embodiment of the present invention.
Figure 5:
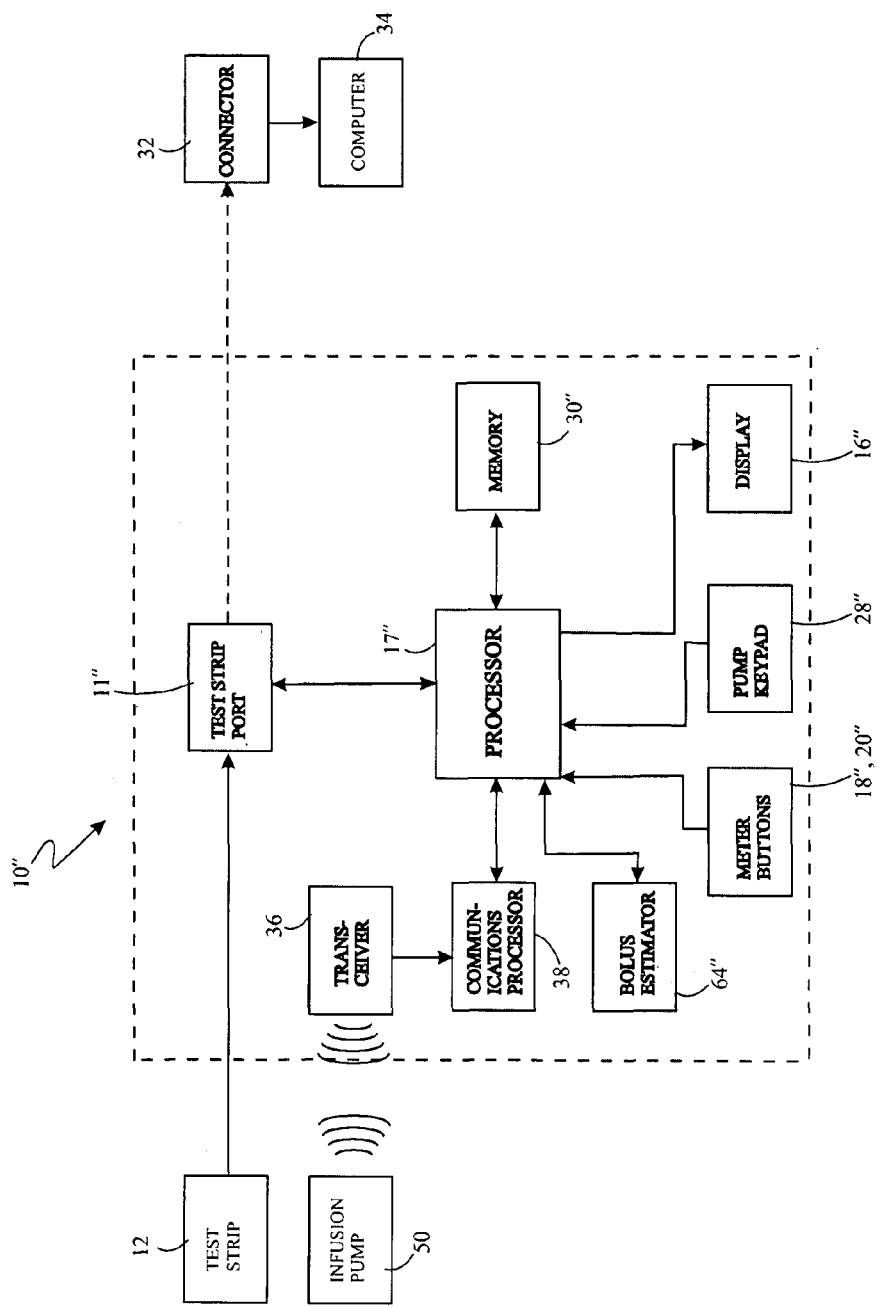
FIG. 5 is a simplified block diagram of a blood glucose monitor in accordance with still another embodiment of the present invention.

The BG meter 10 further includes an additional user input device comprising a keypad 28 with one or more keypad buttons 22, 24, and 26 that are dedicated to remotely controlling the infusion pump 50, for example, via the RF transmitter 15 (or RF transceiver 19 (as shown in FIG. 4b) or 36 (as shown in FIG. 5)), as will be described below. The keypad buttons 22, 24, and 26 may also be used to transmit bolus data to the infusion pump 50 and are labeled 'S' for "suspend", 'B' for "bolus", and 'ACT' for "activate."

In alternative embodiments, other quantities and arrangements of buttons may be included on the meter 10, and the buttons may be labeled other than as illustrated in FIG. 1. Alternatively, the keypad buttons 22, 24, and 26 may be omitted, and the housing buttons 18 and 20 may be used to remotely control the infusion pump 50. On the other hand, the housing buttons 18 and 20 may be omitted, and the keypad buttons 22, 24, and 26 may be used to operate the BG meter 10. Additionally, the user may use other methods to input commands with the BG meter 10, such as selecting a menu item, using the display 16 as a touch screen, or pressing multi-function keys.

In addition to transmitting the bolus amount data to the infusion pump 50, the BG meter 10 also stores the BG measurement and bolus data in the memory 30 of the BG meter 10 for subsequent analysis and review. A history of alarms or error messages generated by the BG meter 10, as well as remote control commands sent to or information received from the infusion pump 50, may also be stored in the memory 30. Further, the user may periodically cause the BG meter 10 to download the stored data through a communication circuit (such as the RF transmitter 15 (or RF transceiver 19 (as shown in FIG. 4b) or 36 (as shown in FIG. 5)), a cable, or a communication station), directly to a computer 34, or alternatively, over the Internet to a remote server for storage. For example, a connector 32 may be inserted into the test strip port 11 to provide a wired connection to a USB, serial, or other port of the computer 34, and data may be downloaded from the BG meter 10 through the connector 32 to the computer 34. The user or a caregiver (e.g., the user's parent, health care professional, educator) can evaluate the user's therapy by accessing the historical BG measurements or bolus data downloaded from the meter 10.

Figure 2:
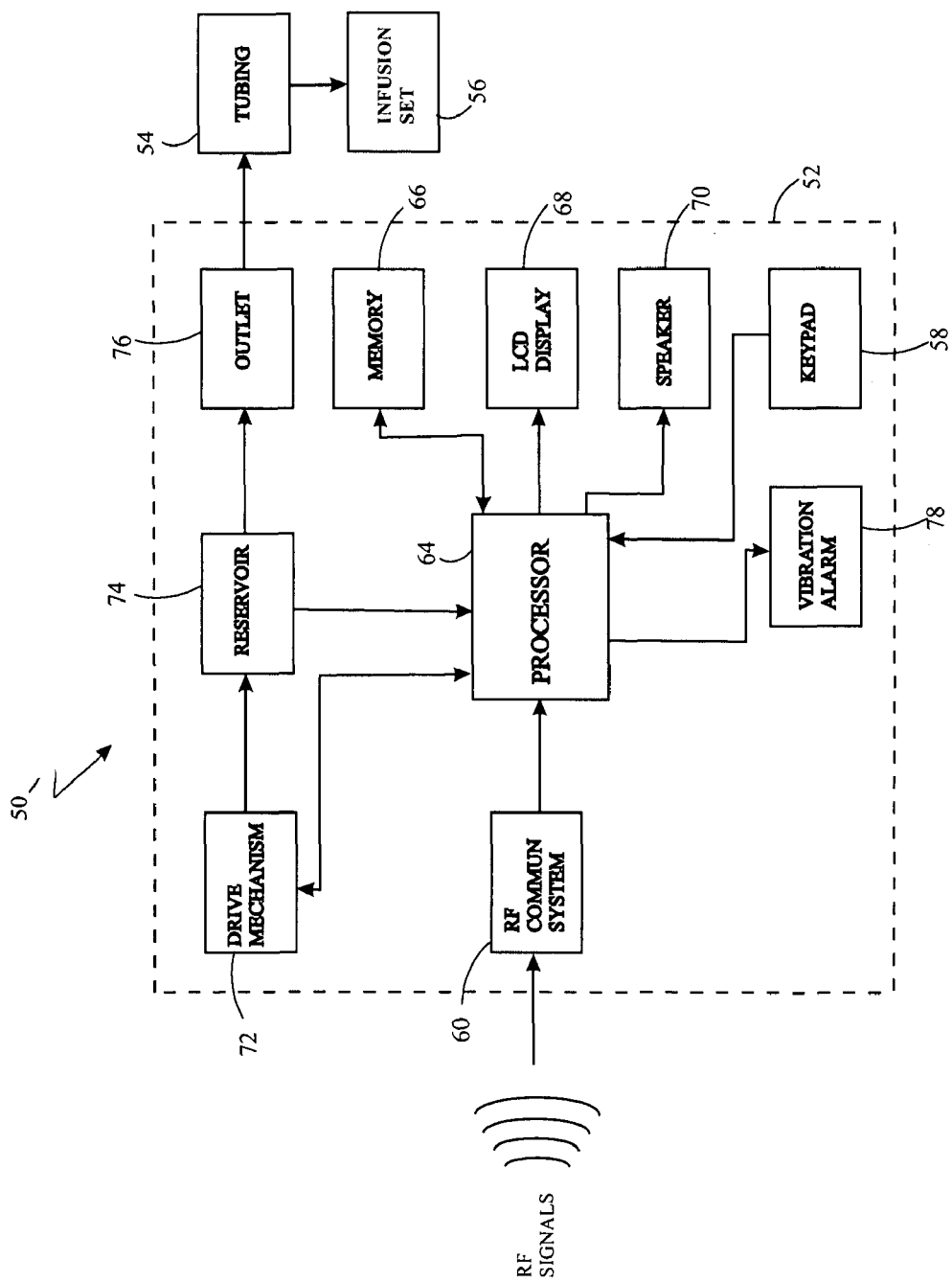
FIG. 2 is a simplified block diagram of an infusion pump in accordance with an embodiment of the present invention.

Referring now to FIGS. 1 and 2, the infusion pump 50 regulates the flow of fluid from the pump, through flexible tubing 54, and into an infusion set 56 that is adhered to the user. Infusion sets that may be used as part of an infusion device are described in, but not limited to, U.S. Pat. Nos. 4,723,947; 4,755,173; 5,176,662; 5,584,813; and 6,056,718, which are herein incorporated by reference. The infusion pump 50 may be of the type described in U.S. Pat. Nos. 4,562,751; 4,685,903; 5,080,653; 5,097,122; 5,505,709; 6,248,093; and 6,554,798, which are herein incorporated by reference. Some infusion pumps are adapted to be carried by a user during his or her daily activities, and thus, may be implanted within the body of the user, or may be external to the body of the user and hand-held or held in a clothing pocket or attached to the body or clothing by straps, adhesives, fasteners, etc.

In alternative embodiments, other devices may be used for delivery or infusion of fluid into a user's body, such as for example, an implantable insulin infusion pump or a system that uses a combination of implantable and external components, an injection pen, an IV meter, etc.

Figure 3A:
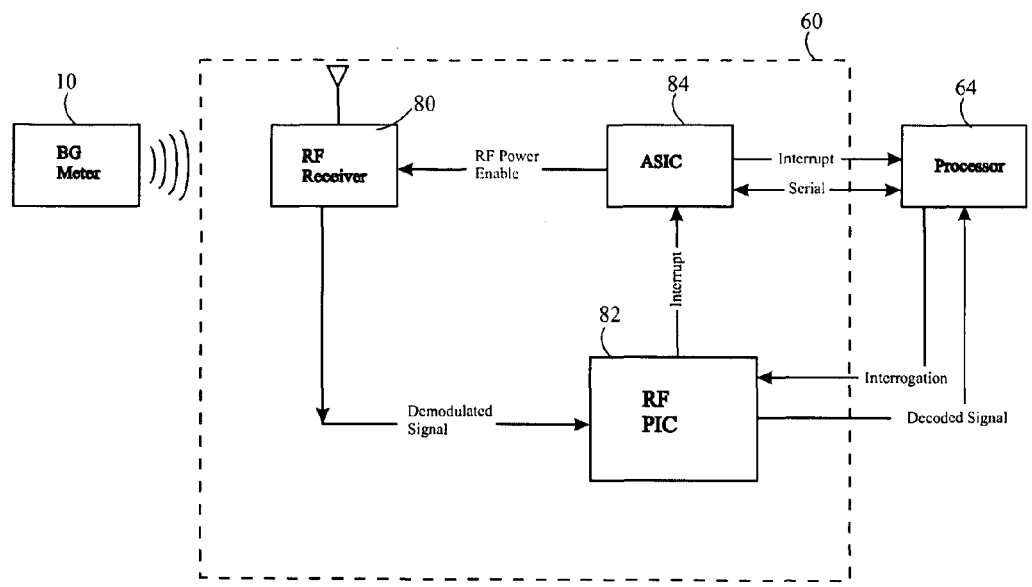
FIG. 3a is a block diagram of an RF communication system in the infusion pump in accordance with an embodiment of the present invention.
Figure 3B:
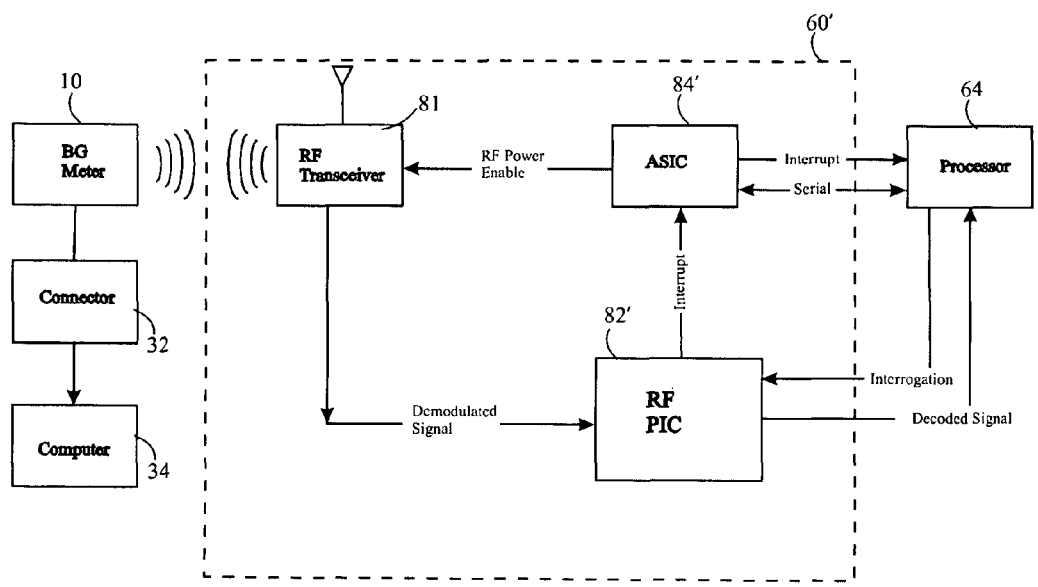
FIG. 3b is a block diagram of an RF communication system in the infusion pump in accordance with another embodiment of the present invention.

Referring still to FIGS. 1 and 2, the infusion pump 50 includes an RF communication system 60 that in turn includes an RF receiver 80, as shown in FIG. 3a. This allows one-way communication from the BG meter 10 (or other external devices such as a remote programmer) to the infusion pump 50. Alternatively, the RF communication system 60' may include an RF transceiver 81, as shown in FIG. 3b, which allows two-way communication between the BG meter 10 and the infusion pump 50.

The RF communication system 60 communicates with a processor 64 contained in a housing 52 of the infusion pump 50. The processor 64 is used to execute programs and control the infusion pump 50, and is connected to an internal memory device 66 that stores programs, history data, user defined information and parameters. The memory device 66 is a ROM and DRAM, but alternatively, the memory device 66 may include other memory storage devices, such as RAM, EPROM, dynamic storage such as flash memory, energy efficient hard-drive, etc.

The infusion pump 50 is preferably programmed through a user input device comprising a keypad 58 on the housing 52, or alternatively, by commands received from an RF programmer (not shown) through the RF communication system 60. The infusion pump 50 may also be programmed by commands that are input using the keypad 28 on the BG meter 10 and received from the BG meter 10, for example, through the RF communication system 60, as will be described below. Feedback by the infusion pump 50 on status or programming changes is shown on a display 68, is provided tactilely with a vibration alarm 78 or audibly through a speaker 70 or other sound generation device. The infusion pump 50 may also provide the user with either an audible alarm or a vibration alarm for notification of a low medication reservoir condition or low battery charge. Alarms may start out at a low decibel or vibration level and escalate until acknowledged by the user. In alternative embodiments, the keypad 58 may include other quantities and arrangements of keys than those illustrated in FIG. 1. Alternatively, the keypad 58 may be omitted, and the display 68 may be used as a touch screen input device. In further alternative embodiments, the keypad 58, display 68, and/or speaker 70 may be omitted, and some or all programming and data transfer may be handled through a communication circuit, i.e. the RF communication system 60.

The processor 64 is also coupled to a drive mechanism 72 that is connected to a fluid reservoir 74 containing fluid. The processor 64 causes the drive mechanism 72 to deliver the fluid through an outlet 76 in the reservoir 74 and housing 52, and then into the user's body through the tubing 54 and the infusion set 56.

In particular embodiments, one-way communication is provided from the BG meter 10 to the infusion pump 50. The BG meter 10 includes the RF transmitter 15 (shown in FIG. 4a), and the infusion pump 50 includes an RF receiver 80 (shown in FIG. 3a). Alternatively, two-way communication may be provided between the BG meter 10 and the infusion pump 50. The RF transmitter 15 in the BG meter 10 is replaced with an RF transceiver 19 (shown in FIG. 4b) or 36 (shown in FIG. 5), and the RF receiver 80 in the infusion pump 50 is replaced with an RF transceiver 81 (shown in FIG. 3b).

The infusion pump 50 provides several programming options, including remote and on-device programming. The infusion pump 50 also can be configured through a communication circuit, such as a cable or communication station, using a computer. Additionally, the infusion pump 50 allows the user to download information in the memory 66 through the communication circuit directly to a computer, or alternatively, over the Internet to a remote server for storage. Further description of a communication station of this general type may be found in U.S. Pat. No. 5,376,070, which is incorporated herein by reference. The user or a caregiver (e.g., the user's parent, health care professional, educator) can evaluate the user's therapy by accessing the historical BG measurements or bolus data downloaded from the BG meter 10 and insulin delivery information downloaded from the pump 50.

Information may also be downloaded from the infusion pump 50 through the RF communication system 60. Referring to FIG. 3b, the RF communication system 60' may include a RF transceiver 81 for transmitting information to and receiving information from external devices. In particular embodiments, an external communication link (not shown) may be connected to a serial, USB, or other port of a computer. Information may be transmitted from the RF transceiver 81 in the infusion pump 50 to an RF transceiver in the external communication link (not shown), which then downloads the information through a wired connection to the computer. During the download process, the communication link may draw power from the computer through the serial, USB, or other port.

In other embodiments, the connector 32 may be inserted into the test strip port 11' of the BG meter 10' to provide a wired connection to a USB, serial, or other port of the computer 34, as shown in FIG. 4b. Information may be transmitted from the RF transceiver 81 in the infusion pump 50 to the RF transceiver 19 in the BG meter 10', and may then be downloaded through the connector 32 to the computer 34. The BG meter 10' merely functions as a "pass through" connection between the infusion pump 50 and the computer 34. During the download process, power may be drawn from a power supply (not shown) for the BG meter 10' (e.g., a battery), or alternatively, from the USB, serial, or other port of the computer 34.

Alternatively, information may be transmitted from the RF transceiver 81 in the infusion pump 50 to the RF transceiver 36 in the BG meter 10", as shown in FIG. 5. The information may be transmitted from the infusion pump 50 to the BG meter 10" at a rate higher than can be handled by the meter processor 17". Accordingly, the BG meter 10" includes a communications microcontroller or processor 38 with a higher processing speed (e.g., 10 MHz) than the meter processor 17" with a lower processing speed (e.g., 1-4 MHz). The transmitted information is first processed by the communications processor 38, then processed by the meter processor 17", and finally downloaded through the connector 32 to the computer 34. Again, the BG meter 10" merely functions as a "pass through" connection between the infusion pump 50 and the computer 34. In alternative embodiments, information may be transmitted from the infusion pump 50 and stored in the memory 30' or 30" of the BG meter 10' or 10" for subsequent downloading from the BG meter 10' or 10" to the computer 34. In further alternative embodiments, information may be transmitted from the infusion pump 50 through the BG meter to the computer 34 using other modes of communication, such as infrared, cable, ultrasonic, sonic, optical, etc.

As previously stated, the BG meter 10 analyzes the blood sample 14 on the test strip 12 to calculate a BG measurement. The BG meter 10 next calculates a bolus amount and communicates the bolus amount to the infusion pump 50. The pump 50 then delivers a bolus of the medication into the user based on the bolus amount data received from the BG meter 10. In particular embodiments, the BG meter 10 automatically communicates the bolus amount data to the pump 50 once the BG meter 10 calculates the bolus amount. Alternatively, the BG meter 10 communicates the bolus amount to the pump 50 upon removal of the test strip 12 from the BG meter 10, or in response to an action by the user.

The BG meter 10 provides notification to the user of several events, including when it is analyzing a blood sample, calculating a bolus amount, and communicating with the pump 50. In particular embodiments, the notification is provided as a status on the display 16. In alternative embodiments, the status is communicated to the user in other ways, such as using one or more light emitting diodes, a vibrator or other tactile device, or one or more audible tones (generated by a speaker, a piezoelectric sound generator or other sound generating device). However, when the BG meter 10 provides continuous or automatic BG measurements, the user is not constantly notified of the status of the calculations and transmissions.

Optionally, the user can direct the BG meter 10 to calculate a bolus estimate amount and/or provide bolus data to the infusion pump 50. User input devices and methods for inputting commands to cause a bolus estimation calculation to be conducted and to transmit bolus data to the infusion pump 50 include: pressing a button, activating a user interface, touching a screen, selecting a menu item, and entering information about a meal such as carbohydrates to be ingested. The BG meter 10 may also re-transmit the bolus amount data to the pump 50 in response to a user action such as pressing a button, selecting a menu item, holding down a button, aligning the BG meter 10 and infusion pump 50, etc. Alternatively, the BG meter 10 may be notified by the infusion pump 50 to re-transmit the bolus amount data.

In particular embodiments, the BG meter 10 increments a counter each time a new bolus amount is calculated and communicated to the pump 50. If a previously calculated and transmitted bolus amount is re-transmitted, then the BG meter 10 does not increment the counter. Each transmission from the BG meter 10 to the infusion pump 50 includes the bolus amount and the counter value. When the infusion pump 50 receives the transmission from the BG meter 10, the pump compares the counter in the new transmission to the counter in a previous transmission. If the counter has not incremented, the infusion pump 50 will ignore the new transmission since it is a duplicate of a previously-received communication. Thus, the infusion pump 50 will activate an insulin delivery only once for each calculated bolus amount.

In alternative embodiments, the BG meter 10 generates a unique code associated with each bolus amount that is communicated to the pump 50. Each transmission from the BG meter 10 to the pump 50 includes the bolus amount and the unique code. The infusion pump 50 stores each code received and ignores any later transmission containing a code that was previously received. In one aspect, the BG meter 10 includes a clock circuit adapted to provide a date and time that may be used to generate the code, or alternatively, the date and time may be used as a counter.

In some embodiments, the BG meter 10 keeps track of the elapsed time between the point when a BG measurement is obtained and when a bolus amount is communicated to the infusion pump 50. The infusion pump 50 includes a clock circuit adapted to provide a date and time, and thus the pump 50 only delivers medication in a bolus amount received from the BG meter 10 if the BG measurement used in the bolus estimation calculation is sufficiently recent in time. Bolus estimations can be at least partially dependent on the difference between the user's present blood glucose level and a desired target blood glucose level. Since a user's BG level varies over time, using a bolus estimation based on an old BG measurement might be inappropriate for the user.

A bolus estimation is expired (and will not be used for delivering medication to a user) when the BG measurement is too old to be considered representative of the user's present BG level. Thus the BG meter 10 will not transmit a bolus amount to the infusion pump 50 if 10 minutes or more have elapsed since the BG measurement was taken. Alternative shorter or longer time delays may be used, however, such as 7 minutes, 5 minutes, 4 minutes, 3 minutes, or 2 minutes, etc., as well as 12 minutes, 15 minutes, 20 minutes, 30 minutes, 1 hour, 1½ hour, 2 hours, 2½ hours, 3hours, 3½ hours, 4 hours, etc. Alternatively, the time required for a BG measurement to expire may be set by the user, a caregiver, a physician, a parent, a guardian, etc. For example, a child's BG level may change more quickly than that of a heavy adult, so the BG meter 10 may be programmed so that BG measurements older than 5 minutes cannot be transmitted to another device. On the other hand, an adult might program the BG meter 10 so that BG measurements expire after 12 minutes.

Alternatively, the infusion pump 50 is programmed to not use a bolus amount if the BG measurement used in the bolus estimation calculation has expired. The infusion pump 50 keeps track of the elapsed time between the point when a new bolus amount is received from the BG meter 10 and when the bolus amount is used to activate an insulin delivery. For example, the infusion pump 50 may be provided the age of the bolus amount it receives. In other words, the elapsed time between when a BG measurement is collected and when the bolus amount is communicated to the infusion pump 50 is transmitted along with each set of bolus data. The pump then can calculate the current age of the bolus amount by adding the age of the bolus amount at the time it was communicated to the time that has passed since the bolus amount was received. Thus, since the infusion pump 50 knows the age of the bolus amount, the infusion pump 50 can reject bolus amounts that are expired. Alternatively, the infusion pump 50 notifies the user if a bolus amount has been received but is expired, before the bolus amount is used to activate a medication delivery. The user may then choose to suspend or activate the bolus delivery.

In particular embodiments, the infusion pump processor 64 causes the drive mechanism 72 to deliver or infuse the fluid into the body of the user according to fluid infusion parameters. For example, the pump can deliver the medication in virtually a single dose, i.e., a "normal bolus." Several minutes may be required to deliver the entire bolus amount depending on other fluid infusion parameters, such as the present basal rate that medication is being delivered, the size of the bolus amount, the delivery location on or in the body, and the maximum rate that the infusion pump 50 can deliver the medication, etc.

The user alternatively may program a bolus type other than a normal bolus. Other delivery profiles or bolus types can include a SQUARE WAVE™ bolus and a DUAL WAVE™ bolus. When a SQUARE WAVE™ bolus is used, the delivery of the bolus is spread at a constant rate over a time period. When a DUAL WAVE™ bolus is used, the user specifies a portion of the bolus amount to be delivered as a normal bolus, and the remaining portion to be delivered as a SQUARE WAVE™ bolus. Other bolus types or profiles can also be used to deliver the bolus amount.

Preferably, the infusion pump 50 automatically activates an insulin delivery almost immediately upon receiving a bolus amount communicated from the BG meter 10, assuming the bolus amount has not expired. Alternatively, the bolus amount can be approved by the user before it is used. The bolus amount is displayed, and the user responds by pressing a button, selecting a menu item, touching a screen, etc., before the bolus amount is used for medication delivery. For example, the bolus amount may be displayed on the display 16 of the BG meter 10 and approved by the user before it is transmitted to the infusion pump 50. Alternatively, the bolus amount may be displayed on the display 68 of the infusion pump 50 and approved by the user before the medication is delivered. Additionally, the user may indicate the bolus type before the bolus is delivered. For example, the user may employ the user input devices on the BG meter 10 to indicate the bolus type and any associated parameters (such as the bolus amount, the bolus delivery duration period, the portion of the bolus amount that is to be delivered immediately, the portion of the bolus amount that is to be delivered over the extended bolus delivery duration period, etc.) along with other parameters that are transmitted to the infusion pump 50 when a bolus amount is to be delivered. Alternatively, the user may use the infusion pump 50 to indicate the bolus type and any associated parameters. The bolus amount may be sent from the BG meter 10 to the infusion pump 50 automatically, whereupon the user input device on the pump 50 may be used to select a bolus type before the bolus is delivered. Additionally, the user can specify a default bolus type.

In some embodiments, the BG meter 10 transmits a bolus amount to the infusion pump 50 using radio frequency (RF) communication. Alternatively, other communication circuits are used, such as infrared (IR), wired, ultrasonic, sonic, optical, etc. Transmissions between the BG meter 10 and the infusion pump 50 may contain unique identifying information associated with the identity of the BG meter 10 and/or the infusion pump 50, such as the BG meter's and/or the infusion pump's serial number, identification number, a password, a code, etc. The identification information may be used to discern between communications that are intended for the respective device (i.e., the BG meter 10 or the pump 50), and those that are not. Alternative identification information or codes can include a password, a bit sequence, a special frequency, timing between communications, etc.

Preferably, the communication system in the BG meter 10 may be deactivated either automatically or by the user, whereupon the meter will not attempt to communicate with other devices. Thus when a new BG measurement is available, the BG meter 10 will not communicate a bolus amount to another device. For example, the RF transmitter 15 (FIG. 4a) or the RF transceiver 19 (FIG. 4b) or 36 (FIG. 5) can be deactivated and reactivated by the user. This can be useful, for example, if the BG meter 10 transmits at frequencies that might disrupt an airplane during take-off or landing. In alternative embodiments, other devices may be used to deactivate and reactivate the BG meter 10 communication system. For example, the infusion pump 50 can be used to deactivate the BG meter's communication system.

Additionally, the BG meter 10 can be programmed to reactivate the communication system after a pre-set duration. When the user deactivates the BG meter's communication system, the user is prompted to enter a duration of time for the communication system to remain deactivated. The communication system will automatically become active at the end of the time period. Alternatively, the user may specify a time of day for the communication system to become active. The user is alerted to review any bolus amounts that were generated while the communication system was deactivated. Then the user can request that they be sent to the infusion pump 50 if desired.

In accordance with one embodiment, two-way communication is used between the BG meter 10 and the infusion pump 50. The infusion pump 50 sends an acknowledge (ACK) message to the BG meter 10 when it receives a transmission. In particular embodiments, the BG meter 10 will not re-transmit (even if requested by the user) if the BG meter 10 has received an ACK from the infusion pump 50. Alternatively, the infusion pump 50 echoes the bolus amount back to the BG meter 10 and waits for a confirmation from the BG meter 10 before delivering the bolus amount. The user is alerted when communication between the BG meter 10 and infusion pump 50 is activated but not functioning properly.

The infusion pump 50 preferably uses power cycling to periodically supply power to its communication system 60. The power cycle is the time period that the communication system 60 is off plus the time period that the communication system is on. In some embodiments, the power cycle is 8 seconds in length. Alternatively, shorter or longer power cycles may be used, such as 4 seconds, 2 seconds, or 1 second, etc., as well as 12 seconds, 15 seconds or 20 seconds, etc.

Additionally, the time period that the communication system 60 is on during each power cycle is preferably 48 milliseconds (ms). Alternatively, the period that the communication system is on during each power cycle can be greater or less than 48 ms, depending on the length of the message to be received, the communication frequency, the speed of the communication system electronics, etc. The BG meter 10 sends repeated signals to the infusion pump 50 for a period longer than the power cycle. Each signal sent from the BG meter 10 to the infusion pump 50 includes a command. The command is preferably short enough to be captured during the on-time of the infusion pump's 50 communication system 60. In accordance with one embodiment, the command is short enough to be captured twice during the infusion pump's 50 communication system 60 on-time.

The time that the infusion pump's 50 communication system 60 must be on to capture the command from the BG meter 10 is short compared to the power cycle, or alternatively is short compared to a string of information. When the infusion pump 50 receives the command, the pump 50 stops power cycling its communication system 60 and turns the system 60 on continuously. Thus short commands may be used to activate the infusion pump's 50 communication system 60 so that one or more longer strings of information may be received by the pump 50.

The infusion pump 50 prepares to receive a string of information that is longer than a command and includes a bolus amount. The string of information may further include an elapsed time since the BG measurement was taken, a bolus type, bolus parameters, a counter, a unique identification code, a date, a time, a serial number, and the time elapsed since the bolus amount was calculated, etc.

The BG meter 10 may transmit a date and time to the infusion pump 50 so that the pump 50 can determine the difference between the BG meter 10 date and time and the pump 50 date and time. Moreover, the pump 50 can reset its clock to correspond to the BG meter 10 clock. Alternatively, the BG meter 10 can use the infusion pump 50 date and time to reset the BG meter 10 clock. In particular embodiments, when the pump 50 acknowledges receipt of information from the BG meter 10, the pump 50 will communicate its current time and date to the meter 10. The meter 10 then resets its clock, if necessary, to correspond to the pump's clock.

The infusion pump 50 preferably returns to power cycling the communication system 60 after information has been received from the BG meter 10. For example, power cycling may be restored after the pump 50 receives a complete signal containing a bolus amount from the BG meter 10. Alternatively, the infusion pump 50 returns to power cycling at a predetermined period after the signal from the BG meter 10 has stopped, or after the commencement of a signal from the BG meter 10.

In alternative embodiments there is no longer string of information that follows a command. Rather, the command itself includes all of the information to be sent to the pump, such as the bolus amount, the bolus type and/or a time parameter, serial number, BG meter counter, etc. Thus the pump does not change from its power cycling routine.

The BG meter 10 is preferably used to control one or more functions of the infusion pump 50. These functions include: bolus delivery (bolus amount, start time, bolus type, duration, maximum bolus amount limit, etc.), basal delivery (profiles, delivery rates, time of day when rates change, maximum basal rate limit, etc.), alarms, user interfaces (turning on or off sound generating devices, vibrator, display, or light, etc.), selection of devices that can communicate with the infusion pump 50, lock-out controls, reservoir seating, reservoir priming, and data download.

Alternative embodiments of a BG meter 10 include one or more indicators and user input devices, such as audible alarms, vibrators, displays (liquid crystal display (LCD), light emitting diodes (LEDs), touch screen, etc.), sound generation devices, keypads, keyboards, buttons, and voice activated controls, etc. In addition to the pump 50, the BG meter 10 can communicate with other devices, such as a computer, PDA, telephone, central server, Internet hardware device, relay, remote alarm or notification device, and a remote controller, etc. The BG meter 10 uses one or more communication circuits or methods to communicate with these other devices, such as RF, infrared (IR), bluetooth, optical, sound, ultrasonic, and wired, etc.

The infusion pump 50 indicates its present function or activity, so that a user can monitor the pump's reaction to commands that it has received, for example, from the BG meter 10. Also, the user may override commands that the infusion pump 50 has received from another device. Alternatively, the infusion pump 50 only communicates with a user through another device, such as via the BG meter 10. Examples of functions/activities indicated to the user include: the delivery of a certain basal profile, the completion of delivery to the user of a certain portion of a bolus, the time period remaining for completing a bolus delivery, the suspension of pump 50 operations, the priming or seating of the pump 50, etc. In one embodiment, the infusion pump 50 communicates to the BG meter 10 the pump status or alarms, such as a fluid path occlusion, an electrostatic discharge alarm, a low battery power level, a low reservoir level, etc.

The user accesses and implements commands using the BG meter 10 through a menu structure shown on the display 16 and navigated by the keypad 28. Alternatively, input devices or other methods are used such as pressing dedicated keys, scribing a command on a screen, touching a touch screen, voice activated commands, etc. Each keystroke on the BG meter 10 is communicated to the infusion pump 50. Alternatively, the BG meter 10 only communicates actionable commands to the infusion pump 50. Thus, the user may press many keystrokes on the BG meter 10 before the BG meter 10 transmits to the pump 50.

For example, the BG meter 10 does not communicate to the infusion pump 50 until the user has stopped pressing keys that might influence the infusion pump 50 function. Thus for example, the user might conduct a programming session on the BG meter 10 to implement a new basal delivery pattern, enter a new serial number of a new device that the infusion pump 50 should respond to, and program a bolus amount. The BG meter 10 would not initiate a transmission to the infusion pump 50 until the user has completed the programming session.

The BG meter 10 identifies the end of a programming session when the user inputs a completion command indicating that the session is complete or commanding the BG meter 10 to initiate the transmission. Alternatively, the BG meter 10 communicates at the end of each actionable command. Alternatively still, the BG meter 10 communicates to the infusion pump 50 whenever the user returns to the main menu, or the BG meter 10 waits a specified delay period after the last keystroke to determine that the user has completed the programming session. The specified delay period may be programmable, or may be a preset period such as 10 seconds, 15 seconds, 30 seconds, 1 minute, etc. The BG meter 10 nevertheless will communicate some commands immediately, such as for example, a suspend command (to stop medication delivery), responses to alarms, or starting a new bolus delivery.

In an alternative embodiment, the meter has a review feature so that the user may scroll through programming steps that are about to be sent to the pump. The user may choose to modify the commands or accept the commands before the meter initiates a transmission to the pump.

As described above, the infusion pump 50 communicates with various external devices, such as the BG meter 10, using RF communication. Additionally, the infusion pump 50 uses power cycling to periodically supply power to its communication system 60. Referring to FIGS. 3a and 3b, to facilitate one-way RF communication, the infusion pump 50 includes a processor 64, a RF receiver 80, a RF microcontroller (or RF programmable integrated circuit—(RF PIC)) 82, and an application specific integrated circuit (ASIC) 84. Alternatively, to facilitate two-way RF communication, the RF receiver 80 may be replaced with an RF transceiver 81, as shown in FIG. 3b. The RF PIC 82 holds a 7-byte word, although in alternative embodiments, it may hold other lengths of data. The processor communicates with the RF PIC 82 and the ASIC 84 using synchronous peripheral interfaces (SPI interfaces).

The RF receiver 80 or RF transceiver 81 receives and demodulates RF signals, extracts a data packet from the RF signal, and passes the data packet to the RF PIC 82. The RF PIC 82 accepts and decodes the data packet and checks for format. If the format of the data packet is valid, the RF PIC 82 sends an interrupt signal to the ASIC 84. When the ASIC 84 receives the interrupt signal from the RF PIC 82, the ASIC 84 sends an interrupt to the processor 64, triggering the processor 64 to notify the RF PIC 82 to pass the contents of its buffer to the processor 64.

The processor 64 acquires the decoded data packet from the RF PIC 82 and evaluates the content, which may include a command or information to be stored. In response to some data packets, the processor 64 may send a command to the ASIC 84 to change the power conditions on the RF receiver 80 or RF transceiver 81. The processor 64 also processes the commands and data received from the BG meter 10, which may result in controlling functions on the infusion pump 50. One of the main tasks for the ASIC 84 is to enable and disable power on the RF receiver 80 or RF transceiver 81. Generally, the ASIC 84 cycles the power on the RF receiver 80 or the RF transceiver 81 to save energy. If commanded by the processor 64, however, the ASIC 84 will enable the RF receiver 80 or the RF transceiver 81 to be powered continuously.

Each RF transmission sent to the infusion pump 50 preferably includes an RF signal header followed by a command packet or an information packet. Since the infusion pump's RF receiver 80 or RF transceiver 81 is likely to wake up in the middle of a command packet, the RF signal header at the start of each transmission helps the infusion pump 50 to synchronize its data sampling and identify the first byte of a new command packet or information packet.

The RF signal header is preferably the same for each transmission, and is transmitted at the start of each RF transmission.

The RF signal header may include two parts: a preamble and a start signature. The preamble is a series of pulses used to train the infusion pump's digital signal sampling, and allows the infusion pump 50 to synchronize its pulse sampling with the pulse bits in the new transmission. The start signature notifies the RF PIC 82 when the first byte of a new packet is starting. Alternatively, the RF signal header may include other data, or the RF signal header may be omitted.

The command packets are 7 bytes in length, and information packets are 71 bytes in length. Alternative embodiments incorporate command packets and information packets of different lengths. The last byte of every command or information packet is an 8-bit cyclic redundancy check (CRC) calculated on all the preceding bytes in the packet. Before a command or information packet is transmitted to the infusion pump 50, it is preferably encoded by the BG meter 10 using a DC balanced encoding scheme, which translates 4 bits of data into 6 for transmission as follows:

| HEX | DC |
|---|---|
| 0 | 010101 |
| 1 | 110001 |
| 2 | 110010 |
| 3 | 100011 |
| 4 | 110100 |
| 5 | 100101 |
| 6 | 100110 |
| 7 | 010110 |
| 8 | 011010 |
| 9 | 011001 |
| A | 101010 |
| B | 001011 |
| C | 101100 |
| D | 001101 |
| E | 001110 |
| F | 011100 |

The result of the encoding is that the 7-byte command packets require transmission of 11 bytes and the 71-byte information packets require transmission of 107 bytes. Upon receipt of the 11-byte or 107-byte packets from the BG meter 10, the RF PIC 82 in the infusion pump 50 decodes the packet into the 7-byte command packet or the 71-byte information packet. The processor 64 checks all packets for valid identification of the infusion pump 50 (e.g., identification or serial number) and CRC. If the infusion pump 50 identification is not valid, the packet is ignored. If the CRC of the first command packet is not valid, the command is ignored. Otherwise, the processor 64 may send a negative acknowledge (NAK) response to any packet with an invalid CRC.

Information packets (71 bytes) are much larger than command packets (7 bytes), and cannot be stored in the RF PIC 82, and thus, cannot be used to "wake up" the pump. Instead, a command packet must be sent to the infusion pump 50 to turn on the pump's RF receiver 80 or RF transceiver 81 and prepare the pump 50 to receive an information packet. While power to the pump's RF receiver 80 or RF transceiver 81 is being cycled, a command packet is repeatedly transmitted from the meter 10 to the pump 50 to activate the pump's RF receiver 80 or RF transceiver 81. If an RF signal (i.e. including the first command packet) is present when the pump's RF receiver 80 or RF transceiver 81 comes on, the pump 50 will attempt to store the contents of the signal in the RF PIC 82.

The processor 64 will verify whether the content of the signal is a valid command packet. If the command packet is valid, then the infusion pump 50 will stop power cycling and power the RF receiver 80 and RF transceiver 81 continuously. Only the first command packet must be transmitted repeatedly. After the RF receiver 80 or RF transceiver 81 is on full-time, other command packets or an information packet can be sent to the infusion pump 50.

The pump 50 preferably recognizes two categories of command packets: remote control or normal bolus commands and bolus estimation or amount commands. Remote control or normal bolus commands directly control the pump's insulin bolus delivery. Bolus estimation or amount commands prepare the pump 50 to receive an information packet containing a new bolus estimate amount.

The pump 50 may receive a normal bolus command from the BG meter 10 or a remote programmer associated with the pump 50. The bolus command preferably includes a type code indicating the type of device transmitting the message (e.g., the BG meter 10 or the remote programmer), unique identifying information about the pump 50 (e.g., serial number, identification number, password, or the like), a key code indicating which bolus command button has been pressed (e.g., button "S" 22, button "B" 24, or button "ACT" 26 on the BG meter 10), and a counter indicating the number of times that the button has been pressed. In alternative embodiments, the bolus command may include other information and/or omit some of this data. When the pump 50 receives the bolus command, the processor 64 filters the command to discern the counter value so that the pump 50 can respond to the number of times the user has pressed the button to adjust a bolus.

The pump 50 may also receive a bolus estimation command from the BG meter 10. The bolus estimation command is transmitted to the pump 50 to prepare the pump 50 to receive an information packet containing a new bolus estimate amount from the BG meter 10. The bolus estimation command preferably includes a type code indicating the type of device transmitting the message (e.g., the BG meter 10), unique identifying information about the pump 50 (e.g., serial number, identification number, password, or the like), and a key code indicating that a new bolus estimate amount is about to be transmitted. In alternative embodiments, the bolus estimation command may include other information and/or omit some of this data.

In response to RF transmissions, the pump 50 typically sends an acknowledge (ACK) response. However, in particular embodiments, the BG meter 10 does not include an RF receiver, and the pump 50 does not include an RF transmitter, and thus, the pump 50 does not send an ACK response if the type code in the command (e.g., bolus or BG measurement command) indicates that the device transmitting the message is the BG meter 10. In alternative embodiments, both the BG meter 10 and the pump 50 may include an RF transceiver (i.e. transceiver 19 (shown in FIG. 4(b)) or 36 (shown in FIG. 5) in the BG meter 10' or 10", and transceiver 81 (shown in FIG. 3(b)) in the infusion pump 50), and thus, the pump 50 may send an ACK response to the BG meter 10.

When the infusion pump 50 receives a command packet from the BG meter 10, the processor 64 will send a data packet through the ASIC 84, commanding the RF receiver 80 or RF transceiver 81 to remain on full-time for a specified number of minutes, to receive other command packets or an information packet. The RF receiver 80 or RF transceiver 81 may return to power cycling after the information packet has been received, a certain period of time after receiving a command (in the event that the anticipated information packet does not arrive), or after the battery in the infusion pump 50 has been removed and replaced.

In an alternative embodiment, the BG meter 10 transmits only normal bolus commands and does not transmit the bolus estimation or amount commands. However, the BG meter 10 transmits the normal bolus commands as a series of commands over a predetermined time period, and this collectively approximates a bolus estimation or amount. The BG meter 10 accomplishes this by converting bolus estimation data into the series of normal bolus commands. Thus by doing so, for example, the SQUARE WAVE™ bolus can be approximated by a series of normal bolus commands transmitted over a predetermined time period that corresponds to the SQUARE WAVE™ bolus time period.

Generally, the infusion pump's RF PIC 82 remains in receive mode unless it has received a command from the processor 64 to transmit, in which case it switches to transmit mode until the transmission is complete. Once the data has been transmitted, the RF PIC 82 automatically returns to receive mode.

Thus according to certain embodiments, there are disclosed methods and apparatuses relating to a physiological monitoring device that conducts a bolus estimation calculation. The monitoring device communicates a bolus amount resulting from the bolus estimation calculation to a medication infusion device, which delivers a bolus of medication to a user based on the communication from the monitoring device. The monitoring device may also be used to control other functions of the medication infusion device based on communications from the monitoring device.

While the description above refers to particular embodiments of the present invention, it will be understood that many modifications may be made without departing from the spirit thereof. The claims are intended to cover such modifications as would fall within the true scope and spirit of the present invention. The presently disclosed embodiments are therefore to be considered in all respects as illustrative and not restrictive, the scope of the invention being indicated by the claims rather than the foregoing description, and all changes which come within the meaning and range of equivalency of the claims are therefore intended to be embraced therein.

What is claimed is:

1. An infusion system for infusing a fluid into a body of a user, the infusion system comprising:
a physiological monitoring device comprising:
a monitoring device processor;
a sensor coupled to the monitoring device processor and adapted to provide an output signal as a function of a concentration of an analyte in the user; and
a monitoring device communication circuit coupled to the monitoring device processor;
wherein the monitoring device processor is adapted to:
determine a first amount of time that has elapsed since the sensor provided the output signal;
determine whether the first amount of time exceeds a predetermined amount of time; and,
if the first amount of time does not exceed a predetermined amount of time,
calculate an amount of the fluid to be infused into the user's body based upon the output signal, and
cause the monitoring device communication circuit to transmit a first set of data indicative of the calculated amount of the fluid to be infused;
wherein the monitoring device communication circuit does not transmit a set of data indicative of a calculated amount of fluid to be infused into the user's body based upon the output signal if the first amount of time exceeds the predetermined amount of time; and
a medication infusion device comprising:
an infusion device processor;
a drive mechanism coupled to the infusion device processor and adapted to infuse the fluid into the body of the user; and
an infusion device communication circuit coupled to the infusion device processor and adapted to receive the first set of data from the monitoring device communication circuit;
wherein the infusion device processor is adapted to cause the drive mechanism to infuse the fluid into the body of the user in accordance with the first set of data indicative of the calculated amount of the fluid to be infused; and
wherein the physiological monitoring device is adapted to be carried by the user on an exterior of the body of the user and the medication infusion device is adapted to be carried by the user on an exterior of the body of the user.

2. The system of claim 1, wherein the infusion device processor causes the drive mechanism to infuse the fluid in accordance with the first set of data automatically after receipt of the first set of data by the infusion device communication circuit.

3. The system of claim 1 for use with a test strip, wherein the physiological monitoring device is a blood glucose test strip meter adapted to analyze a test strip exposed to a discrete sample of the analyte of the user to provide a discrete measurement of the analyte in the user, and wherein the medication infusion device is an insulin infusion pump.

4. The system of claim 1, wherein the monitoring device communication circuit includes one of a transmitter and a transceiver, and wherein the infusion device communication circuit includes one of a receiver and a transceiver.

5. The system of claim 1, wherein the monitoring device further comprises an indicator coupled to the monitoring device processor and adapted to provide a notification of at least one event of the group consisting of: the measuring of the output signal produced by the sensor, the calculating of the amount of the fluid, and the transmitting of the first set of data by the monitoring device communication circuit.

6. The system of claim 5 wherein the indicator includes at least one of a vibration alarm, a sound generation device, a panel adapted to display text, and a LED.

7. The system of claim 1, wherein the monitoring device further comprises an indicator coupled to the monitoring device processor and adapted to provide a notification of the completion of at least one event of the group consisting of: the measuring of the output signal produced by the sensor, the calculating of the amount of the fluid, and the transmitting of the first set of data by the monitoring device communication circuit.

8. The system of claim 1 wherein the monitoring device further comprises a user input device for inputting a command and wherein the monitoring device communication circuit transmits the first set of data in response to the command from the input device.

9. The system of claim 1 wherein the monitoring device further comprises a user input device for inputting a command and wherein the predetermined amount of time is established in response to the command from the input device.

10. The system of claim 1 wherein the monitoring device further comprises:
an indicator coupled to the monitoring device processor and adapted to provide a display of the amount of the fluid; and
a user input device for inputting commands;
wherein the monitoring device processor is further adapted to cause the monitoring device communication circuit to transmit the first set of data in response to a first command from the input device.

11. The system of claim 10 wherein the monitoring device further comprises a monitoring device memory coupled to the monitoring device processor and adapted to store at least two fluid infusion parameters, and wherein the monitoring device processor is further adapted to:
retrieve one of the at least two fluid infusion parameters from the memory in response to a second command from the input device associated with a selection by the user of the one of the at least two fluid infusion parameters; and
cause the monitoring device communication circuit to transmit the one of the at least two fluid infusion parameters.

12. The system of claim 1 wherein the infusion device further comprises:
an indicator coupled to the infusion device processor and adapted to provide a display of the amount of the fluid; and
a user input device for inputting a command;
wherein the infusion device processor is further adapted to cause the drive mechanism to infuse the fluid into the body of the user in accordance with the first set of data in response to the command from the input device.

13. The system of claim 1 wherein the infusion device further comprises:
an indicator coupled to the infusion device processor and adapted to provide a display of the amount of the fluid;
a user input device for inputting commands; and
an infusion device memory coupled to the infusion device processor and adapted to store at least two fluid infusion parameters;
wherein the infusion device processor is further adapted to:
retrieve one of the at least two fluid infusion parameters from the memory in response to a command from the input device associated with a selection by the user of the one of the at least two fluid infusion parameters; and
cause the drive mechanism to infuse the fluid into the body of the user in accordance with the one of the at least two fluid infusion parameters.

14. The system of claim 1 wherein the monitoring device further comprises a monitoring device memory coupled to the monitoring device processor and adapted to store a first identification value associated with the identity of the infusion device,
wherein the monitoring device processor is further adapted to cause the monitoring device communication circuit to transmit the first identification value;
wherein the infusion device communication circuit is further adapted to receive the first identification value; and
wherein the infusion device processor is further adapted to compare the first identification value with a stored identification value and to cause the drive mechanism to infuse the fluid into the body of the user in accordance with the first set of data if the first identification value is equal to the stored identification value.

15. The system of claim 1, wherein the monitoring device further comprises a monitoring device clock circuit adapted to provide a monitoring device date and time;
wherein the infusion device further comprises an infusion device clock circuit adapted to provide an infusion device date and time;
wherein the monitoring device processor is further adapted to cause the monitoring device communication circuit to transmit the monitoring device date and time;
wherein the infusion device communication circuit is further adapted to receive the monitoring device date and time; and
wherein the infusion device processor is further adapted to alter the infusion device date and time to be equal to the monitoring device date and time.

16. The system of claim 1, wherein the monitoring device further comprises a monitoring device clock circuit adapted to provide a monitoring device date and time;
wherein the infusion device further comprises an infusion device clock circuit adapted to provide an infusion device date and time;
wherein the infusion device processor is further adapted to cause the infusion device communication circuit to transmit the infusion device date and time;
wherein the monitoring device communication circuit is further adapted to receive the infusion device date and time; and
wherein the monitoring device processor is further adapted to alter the monitoring device date and time to be equal to the infusion device date and time.

17. The system of claim 1, wherein the monitoring device further comprises a user input device for inputting a first command and a second command,
wherein the monitoring device processor is further adapted to:
receive the first and the second commands; and
cause the monitoring device communication circuit to discontinue transmissions in response to the first command and to resume transmissions in response to the second command; and
wherein the monitoring device processor is adapted to cause the monitoring device communication circuit to transmit the first set of data after receipt of the second command.

18. The system of claim 1 wherein the monitoring device further comprises:
a user input device for inputting a command; and
a memory coupled to the monitoring device processor;
wherein the monitoring device processor is further adapted to:
cause the memory to store a value associated with a duration of time established in response to the command from the input device; and
cause the monitoring device communication circuit to discontinue transmissions until the duration of time has elapsed; and
wherein the monitoring device processor is adapted to cause the monitoring device communication circuit to transmit the first set of data after the duration of time has elapsed.

19. The system of claim 1 wherein the monitoring device further comprises:
- a user input device for inputting a command; and
- a memory coupled to the monitoring device processor;
- wherein the monitoring device processor is further adapted to:
  - cause the memory to store a value associated with a date and time established in response to the command from the input device; and
  - cause the monitoring device communication circuit to discontinue transmissions until the date and time have arrived;
- wherein the monitoring device processor is adapted to cause the monitoring device communication circuit to transmit the first set of data after the date and time have arrived.

20. The system of claim 1 wherein the infusion device further comprises a user input device for inputting commands,
- wherein the infusion device processor is further adapted to cause the infusion device communication circuit to transmit a first command from the input device and a second command from the input device;
- wherein the monitoring device communication circuit is further adapted to receive the first command and the second command;
- wherein the monitoring device processor is further adapted to cause the monitoring device communication circuit to discontinue transmissions in response to the first command and to resume transmissions in response to the second command; and
- wherein the monitoring device processor is adapted to cause the monitoring device communication circuit to transmit the first set of data after receipt by the monitoring device communication circuit of the second command.

21. The system of claim 1 wherein the monitoring device processor is further adapted to cause the monitoring device communication circuit to transmit a first command repeatedly for a plurality of transmissions;
- wherein the infusion device communication circuit is further adapted to receive the first command; and
- wherein the infusion device processor is further adapted to:
  - cause power to the infusion device communication circuit to be cycled whereby the power is removed from the infusion device communication circuit for a first time period and is restored to the infusion device communication circuit for a second time period; and
  - cause the power to the infusion device communication circuit to be restored and the power cycling to be discontinued if the first command has been received.

22. The system of claim 21 wherein the infusion device processor is further adapted to resume the cycling of the power to the infusion device communication circuit after receipt of the first set of data following the receipt of the first command.

23. The system of claim 21 wherein the infusion device processor is further adapted to resume the cycling of the power to the infusion device communication circuit after a predetermined period of time has elapsed after receipt of the first set of data following the receipt of the first command.

24. The system of claim 21 wherein the monitoring device processor is further adapted to cause the monitoring device communication circuit to transmit a second command after completion of the transmission of the first set of data;
- wherein the infusion device communication circuit is further adapted to receive the second command; and
- wherein the infusion device processor is further adapted to resume the cycling of the power to the infusion device communication circuit if the second command has been received.

25. The system of claim 1 wherein the first set of data is further indicative of at least one of a medication delivery profile, a counter value, an elapsed time since the output signal was provided, an identification value associated with the identification of the infusion device, and a date and time of transmission of the first set of data.

26. The system of claim 1 wherein the monitoring device further comprises a user input device for inputting a command,
- wherein the monitoring device processor is further adapted to cause the monitoring device communication circuit to transmit the command from the input device;
- wherein the infusion device communication circuit is adapted to receive the command; and
- wherein the infusion device processor is adapted to control the infusion device in accordance with the command.

27. The system of claim 26 wherein the control of the infusion device comprises one of a medication delivery start time, a medication delivery profile, a medication delivery rate, a medication delivery amount, a cessation of a medication delivery, an activation of an alarm, a cessation of an alarm, a display of a text message, and a download of data.

28. The system of claim 26 wherein the user input device comprises one of a button, a touch screen, a voice-activated device, and a menu structure shown on a display panel that is navigated by a keypad.

29. The system of claim 1 wherein the monitoring device further comprises a user input device for inputting a plurality of commands during a time period, said plurality of commands comprising a programming session,
- wherein the monitoring device processor is further adapted to cause the monitoring device communication circuit to transmit the plurality of commands if the time period has elapsed;
- wherein the infusion device communication circuit is further adapted to receive the plurality of commands; and
- wherein the infusion device processor is further adapted to control the infusion device in accordance with the plurality of commands.

30. The system of claim 1 wherein the monitoring device further comprises a user input device for inputting a plurality of commands corresponding to a programming session and for inputting a completion command corresponding to a completion of the programming session, and
- wherein the monitoring device processor is further adapted to cause the monitoring device communication circuit to transmit the plurality of commands if the completion command from the input device has been inputted;
- wherein the infusion device communication circuit is further adapted to receive the plurality of commands; and
- wherein the infusion device processor is further adapted to control the infusion device in accordance with the plurality of commands.

31. The system of claim 1 wherein the monitoring device further comprises a user input device for inputting a plurality of commands corresponding to a programming session, wherein the monitoring device processor is further adapted to determine a calculated time period having a beginning time and an ending time,
  the beginning time corresponding to the entry of one of the plurality of commands, and
  the ending time corresponding to the earlier of a first event and a second event, the first event being the entry of a subsequent one of the plurality of commands, and the second event being the elapse of a predetermined amount of time; and
wherein the monitoring device processor is further adapted to cause the monitoring device communication circuit to transmit the plurality of commands if the calculated time period exceeds the predetermined amount of time;
wherein the infusion device communication circuit is further adapted to receive the plurality of commands; and
wherein the infusion device processor is further adapted to control the infusion device in accordance with the plurality of commands.

32. The system of claim 1 wherein the monitoring device further comprises an indicator coupled to the monitoring device processor,
  wherein the infusion device processor is further adapted to cause the infusion device communication circuit to transmit a second set of data corresponding to an infusion device status;
  wherein the monitoring device communication circuit is further adapted to receive the second set of data; and
  wherein the monitoring device processor is further adapted to cause the indicator to display the infusion device status in accordance with the second set of data.

33. A physiological monitoring device adapted for communications with a medication infusion device carried by a user on an exterior of a body of the user for infusing a fluid into the body of the user, the physiological monitoring device comprising:
  a housing adapted to be carried by the user on an exterior of the body of the user;
  a monitoring device processor enclosed within the housing;
  a sensor coupled to the monitoring device processor and adapted to provide an output signal as a function of a concentration of an analyte in the user; and
  a monitoring device communication circuit coupled to the monitoring device processor;
  wherein the monitoring device processor is adapted to:
    determine a first amount of time that has elapsed since the sensor provided the output signal;
    determine whether the first amount of time exceeds a predetermined amount of time; and,
    if the first amount of time does not exceed a predetermined amount of time,
      calculate an amount of the fluid to be infused into the user's body based upon the output signal, and
      cause the monitoring device communication circuit to transmit a first set of data for reception by the infusion device, the first set of data being indicative of the calculated amount of the fluid to be infused and adapted to cause the infusion device to infuse the calculated amount of the fluid into the body of the user in accordance with the first set of data;
  wherein the monitoring device communication circuit does not transmit a set of data indicative of a calculated amount of fluid to be infused into the user's body based upon the output signal if the first amount of time exceeds the predetermined amount of time.

34. The monitoring device of claim 33, wherein the monitoring device is a blood glucose test strip meter adapted to analyze a test strip exposed to a discrete sample of the analyte of the user to provide a discrete measurement of the analyte in the user, and wherein the medication infusion device is an insulin infusion pump.

35. The monitoring device of claim 34, wherein the monitoring device communication circuit includes one of a transmitter and a transceiver.

36. The monitoring device of claim 33, wherein the monitoring device further comprises an indicator coupled to the monitoring device processor and adapted to provide a notification of at least one event of the group consisting of: the measuring of the output signal produced by the sensor, the calculating of the amount of the fluid, and the transmitting of the first set of data by the monitoring device communication circuit.

37. The monitoring device of claim 33, wherein the monitoring device further comprises an indicator coupled to the monitoring device processor and adapted to provide a notification of the completion of at least one event of the group consisting of: the measuring of the output signal produced by the sensor, the calculating of the amount of the fluid, and the transmitting of the first set of data by the monitoring device communication circuit.

38. The monitoring device of claim 33, wherein the monitoring device further comprises a user input device for inputting a command and wherein the monitoring device processor is adapted to cause the monitoring device communication circuit to transmit the first set of data in response to the command from the input device.

39. The monitoring device of claim 33 wherein the infusion device is adapted to be controlled by a command and wherein the monitoring device further comprises:
  a user input device for inputting the command,
  wherein the monitoring device processor is further adapted to cause the monitoring device communication circuit to transmit the command for reception by the infusion device.

40. The monitoring device of claim 39 wherein the user input device comprises one of a button, a touch screen, a voice-activated device, and a menu structure shown on a display panel that is navigated by a keypad.

* * * * *